(12) United States Patent
Corbett et al.

(10) Patent No.: US 7,709,250 B2
(45) Date of Patent: May 4, 2010

(54) CONTINUOUS FLOW THERMAL DEVICE

(75) Inventors: John Michael Corbett, Sanctuary Cove (AU); John Michael Corbett, Jr., Bellevue Hill (AU)

(73) Assignee: Corbett Research Pty Ltd, Mortlake (AU)

( * ) Notice: Subject to any disclaimer, the term of this patent is extended or adjusted under 35 U.S.C. 154(b) by 938 days.

(21) Appl. No.: 11/149,217

(22) Filed: Jun. 10, 2005

(65) Prior Publication Data

US 2005/0282206 A1  Dec. 22, 2005

Related U.S. Application Data

(63) Continuation of application No. PCT/AU02/01112, filed on Aug. 16, 2002.

(51) Int. Cl.
*C12M 1/34* (2006.01)
*C12M 3/00* (2006.01)
*C12M 1/00* (2006.01)
*B28B 1/00* (2006.01)
*B29C 45/40* (2006.01)
*B01L 3/00* (2006.01)

(52) U.S. Cl. .............. 435/303.1; 435/287.2; 435/288.3; 425/286; 422/99

(58) Field of Classification Search .............. 435/288.3, 435/303.1, 287.2; 422/99; 425/286
See application file for complete search history.

(56) References Cited

U.S. PATENT DOCUMENTS 3,664,178 A * 5/1972 Spergel et al. ................ 73/19.1

(Continued)

FOREIGN PATENT DOCUMENTS

JP  2001145486 A  5/2001

(Continued)

OTHER PUBLICATIONS

Pirulli D., Boniotto, M., Puzzer D, Spano a., Amoroso A. and Crovella S. Flexibility of Melting temperature Assay for Rapid Detection of Insertions, Deletions, and Single-point Mutations of the AGXT Gene responsible for Type 1 Primary Hyperoxaluria. 2000. Clinical Chemistry, v.46, No. 11 p. 1842-1844.*

(Continued)

*Primary Examiner*—Walter D Griffin
*Assistant Examiner*—Lydia Edwards
(74) *Attorney, Agent, or Firm*—Steptoe & Johnson LLP (57) ABSTRACT

The present invention provides a thermal cycling device including: a heat exchanger body (3) having a longitudinal axis and longitudinally divided to provide at least two segments which are able to be heated to different temperatures so that said body has peripheral surfaces of different temperatures; a conduit (2) extending about said body so as to be in thermal contact with said peripheral surfaces; a first delivery device to deliver a first fluid to said conduit to cause said fluid to pass therealong and therefore change in temperature as the fluid passes said segments; and a second delivery device to deliver a second fluid to said conduit so as to flow with said first liquid and therefore also change in temperature. The fluid then leaves the device by conduit (4). The invention also is directed to an injector means for use in the thermal cycling device of this invention, comprising: a septum (26); a needle (20) which is able to pierce the septum; a reservoir (27) in fluid contact with septum (26) having an inlet (28) and an outlet (30); wherein when in use, the needle is urged through the fluid in said reservoir and then through the septum while continually purging the reservoir with said purge fluid. The present invention also includes a scanning detector (5) fitted to the outside of the heat exchange body (3) which monitors the course of reaction inside the conduit (2).

46 Claims, 6 Drawing Sheets

U.S. PATENT DOCUMENTS

| | | | |
|---|---|---|---|
| 5,176,203 A * | 1/1993 | Larzul | 165/61 |
| 5,270,183 A * | 12/1993 | Corbett et al. | 435/91.2 |
| 5,627,026 A * | 5/1997 | O'Connor et al. | 435/5 |
| 6,303,343 B1 * | 10/2001 | Kopf-Sill | 435/91.1 |

FOREIGN PATENT DOCUMENTS

| | | |
|---|---|---|
| WO | WO 98/09728 | 3/1998 |
| WO | WO 98/16313 | 4/1998 |
| WO | WO 00/69560 | 11/2000 |
| WO | WO 01/07159 | 2/2001 |

OTHER PUBLICATIONS

JP 2001-145486. Machine translation p. 1-16.*

* cited by examiner

CONTINUOUS FLOW THERMAL DEVICE

This application is a continuation of International Application No. PCT/AU02/01112, filed on Aug. 16, 2002, which designates the United States and claims priority to AU Patent Application No. PR 7071, filed on Aug. 16, 2001.

TECHNICAL FIELD

The present invention relates to a device which is able to control and vary in a cyclical manner, or in a progressive manner, the temperature of a fluid in a tube or is able to maintain fluid in a tube at a constant temperature; and is particularly applicable to monitoring the course of a reaction by real time scanning. It is applicable to a device for amplifying nucleic acids when amplification takes place by use of reactions such as the polymerase chain reaction, the ligase chain reaction and the like, when the device is used to vary temperature; and is also applicable to isothermal reactions when the device maintains the temperature at a constant level. Specifically, the present invention, when it relates to a temperature cycling device, takes reactants through different temperatures in a cyclical fashion where it is necessary that the temperature change be achieved accurately and rapidly. Importantly, the present invention provides a system where the reaction, whether carried out in a cyclical manner, a progressive manner, or isothermally, can be monitored by real time monitoring. For example, in the case of cyclic reactions, it is possible to monitor the course of a reaction at each cycle.

BACKGROUND OF THE INVENTION

When devices for amplification of nucleic acids using the polymerase chain reaction ("PCR") were first developed, it was necessary to allow the amplification reaction to occur for one cycle at a temperature of approximately 37° C.; to then separate the resulting double stranded DNA by heating to approximately 100° C.; and finally to cool the mixture of separated DNA strands and add more polymerase to cause another cycle of amplification to take place. It soon became clear that these devices were cumbersome to use due to the constant need to cool the individual reaction mixtures to about 37° C. and add fresh polymerase enzyme, due to its destruction when the temperature had been raised to about 100° C.

The advent of thermostable nucleic acid polymerases changed the situation dramatically. These enzymes are stable at about 95° C. and therefore it was not necessary to replace these enzymes after heating to separate the two strands of DNA. Thus, devices which took advantage of a thermostable nucleic acid polymerase were developed.

Current technology uses 96 and 384 well plates real-time instruments to attain high throughput, coupled with automated robotic systems to load, seal and transfer plates to and from real-time thermal cyclers. Using this technology the throughput is limited by the run time of a 384 well cycler which is approx 90 minutes and so equates to 16 runs in 24 hours at 384 well samples and equals approx 6,000 samples.

These robotic systems are physically large, prone to break down, expensive (about $A240,000 as at 2001) and require constant routine maintenance.

Difficulties encountered with these current devices were in part addressed by the invention described and claimed in U.S. Pat. No. 5,270,183 (U.S. '183) which was developed by one of the present inventors (Corbett, Snr) and two others, Reid and Riggs, the contents of which is incorporated herein by reference. In essence, that invention was directed to the reactants travelling through a continuous tube which was subjected to varying temperatures by coiling the tube around substantially drum shaped bodies held at varying temperatures. In order to prevent cross contamination between samples, the reaction mixture was injected into a stream of carrier fluid which separated separate reaction mixtures and passed through two or three separate heating zones. This arrangement allows sequential processing of a number of samples. The carrier fluid and reaction mixture are immiscible. The result of this is that each sample is cleanly separated from the preceding and following sample by segments of carrier fluid.

DISCLOSURE OF THE INVENTION

Although the device described in U.S. '183 was an advance over previous such devices, a major drawback was that since the heating zones are separate it is not convenient to conduct real time monitoring of the course of a reaction. In addition, having heating zones which are separated from each other physically tends to be cumbersome. In order to address these disadvantages, the present device was developed. The device as described below and claimed thus is suitable for use in situations where it is necessary to follow the course of a reaction by real time monitoring. It also has wider applicability than nucleic acid amplification and may be used in any situation where a chemical reaction is performed where the temperature is taken through one or more cycles, for example in carrying out antibody-antigen binding reactions. It is also applicable to situations where it is necessary to hold the temperature at a constant value. Thus, there is a variety of situations where the device of the present invention is applicable and set out below are various embodiments of the invention which illustrate this.

Therefore, in accordance with a first aspect of this invention there is provided a thermal cycling device including: a heat exchanger body having a longitudinal axis and longitudinally divided to provide at least two segments which are able to be heated to different temperatures so that said body has peripheral surfaces of different temperatures; a conduit extending about said body so as to be in thermal contact with said peripheral surfaces; a first delivery device to deliver a first fluid to said conduit to cause said fluid to pass therealong and therefore change in temperature as the fluid passes said segments; and a second delivery device to deliver a second fluid to said conduit so as to flow with said first liquid and therefore also change in temperature.

In one preferred aspect of this invention, the body is longitudinally divided so that said segments and surfaces are longitudinally extending, and said conduit extends angularly about said body relative to said axis.

This aspect is applicable, for example to the polymerase chain reaction (PCR) and ligase chain reaction (LCR).

In a preferred form of this aspect, the first fluid comprises a sample to be analysed and reagents used in the analysis and the second fluid comprises a transport fluid. The sample to be analysed is a nucleic acid and may be DNA or RNA. The reagents used in the analysis are well known in the art, including for example nucleic acid polymerase, for example Taq polymerase.

In accordance with the second aspect of this invention there is provided a thermal cycling device including: a heat exchanger body having a longitudinal axis and transversely divided to provide at least two segments which are able to be heated to different temperatures so that said body has peripheral surfaces of different temperatures; a conduit extending about said body so as to be in thermal contact with said peripheral surfaces; a first delivery device to deliver a first fluid to said conduit to cause said fluid to pass therealong and therefore change in temperature as the fluid passes said segments; and a second delivery device to deliver a second fluid to said conduit so as to flow with said first liquid and therefore also change in temperature.

In another preferred aspect of this invention, the body is transversely divided relative to said axis so that said segments and surfaces extend angularly about said axis, and said conduit extends longitudinally of said body relative to said axis.

This aspect is applicable where the temperature is changed in a progressive manner from one temperature to another temperature, for example, to DNA melt detection studies.

In a preferred form of this aspect, the first fluid comprises a sample to be analysed and the second fluid comprises a transport fluid. The sample to be analysed is a nucleic acid and may be DNA or RNA. The reagents used in the analysis are well known in the art.

In accordance with a third aspect of this invention there is provided an isothermal device including: a heat exchanger body having a longitudinal axis and a peripheral surface and means for maintaining the temperature of said peripheral surface at a constant selectable temperature; a conduit extending about said body so as to be in thermal contact with said peripheral surface; a first delivery device to deliver a first fluid to said conduit to cause said fluid to pass therealong and therefore change in temperature as the fluid passes said peripheral surface; and a second delivery device to deliver a second fluid to said conduit so as to flow with said first liquid and therefore also change in temperature.

This aspect is applicable, for example when conducting antibody-antigen binding reactions. Thus, in this aspect, the heat exchanger may be a solid body which can maintain a fixed, selectable temperature.

In a preferred form of this aspect, the first fluid comprises an antibody and antigen to said antibody and the second fluid comprises a transport fluid.

It is preferred that the conduit which extends about the heat exchanger body in the three aspects above is disposed in a series of consecutive windings and that the heat exchanger body is solid.

In a particularly preferred embodiment of this invention the device of each embodiment also comprises a scanning detector which is able to monitor the progress of a chemical reaction occurring in the conduit. The scanning detector is further described below. With the addition of this scanning detector, it is possible, in each of the above-described embodiments to monitor the course of a reaction at any point on the outside of the thermal cycling device or isothermal device.

Thus, in the case of the device being used for a PCR, the heat exchanger body is in the form of a cylinder or equivalent shape, it may be divided into "pie" shaped segments each being at a different temperature (typically about 94° C., 55° C., 72° C.) so that as the samples migrate around one turn of the spiral, the temperature in the fluid is cycled to those temperatures corresponding to the "pie" segment of the body.

Alternatively, the heat exchanger body may have a temperature gradient applied across it from one end to the opposite end. In the case of a cylinder, the temperature gradient would be set from one flat surface to the opposite flat surface to the top flat surface so that as the samples migrate around the spiral the temperature is gradually increased or decreased.

The heat exchanger body may also be maintained at a uniform temperature, where the temperature may suitably be maintained at any temperature from 0-100° C.

Each of the different temperatures may be achieved by standard electrical heating and optionally air cooling to adjust the temperature; by circulating fluid at a particular temperature; or by the use of Peltier devices. It is particularly preferred that Peltier devices be used since the use of such devices allows a more accurate temperature selection.

An important aspect of temperature control in the first aspect is based on the fact that fluid in the conduit passes from a segment at 95° C. to a segment at 55° C. The effect of this is that in the 55° C. segment, fluid would tend to heat the surface of the 55° C. segment. It is for this reason that air cooling may be necessary depending on the speed of fluid in the conduit and hence transfer of heat from the fluid back to the segment at the lower temperature of 55° C.

When the heat exchanger body is substantially cylindrically shaped, the conduit is preferably disposed in the form of a series of coils arranged in a spiral fashion around the cylinder.

Thus, when the device is used to conduct the PCR, the device of the first embodiment is particularly applicable and each turn of the spiral represents one cycle in the PCR and it is therefore possible to choose the number of cycles by equating this to the number of turns of conduit. Typically, the number of turns is 35-60. Preferably, the device comprises 60 turns which in practice allows a choice of scanning as many turns as required.

When the device is used for PCR and LCR for example and any other reaction where a temperature may be reached such that the fluid in the conduit may degass, it is important to provide a positive back pressure to prevent vaporisation within the fluid stream. Degassing will cause bubbles in the tubing and will interfere with the flow characteristics of the reaction mixture. Thus, degassing will lead to the formation of small bubbles which may break away from the sample and possibly move through the oil carrier under gravity and contaminate a neighbouring sample. The back pressure which is applied should be between about 300 and about 700 kPa and may be achieved by methods known in the art. For example, it may be achieved by use of a spring and ball device at the fluid outlet where adjusting the tension of the spring sets the pressure.

The conduit is suitably tubing which has the following properties: (1) It is able to conduct heat from the heat exchanger body to fluid in the conduit efficiently so that a change in temperature in a particular portion of the heat exchanger body accurately causes a change in temperature in the conduit adjacent that portion of the heat exchanger body which in turn causes a change in temperature in the fluid inside the corresponding interior portion of the conduit. (2) The interior surface of the conduit is hydrophobic so that the reaction mixture has no affinity for the interior surface of the tubing. Suitably, the conduit is PTFE tubing or similar.

The fluid present in the conduit is any fluid where the temperature needs to be controlled precisely and accurately and either cyclically, progressively or isothermally. Preferably, the fluid comprises a reaction mixture containing reagents to amplify one or more nucleic acids and a sample containing one or more nucleic acids. The nucleic acids to be amplified are either RNA or DNA and the enzymes used in the reaction mixture are any enzymes well known in this art. For example, DNA polymerases may suitably be used to amplify DNA and preferably thermostable DNA polymerases are particularly applicable in the reactions carried out in the device of this invention. Suitably, the fluid may be divided into two streams as set out in the first embodiment of the invention described above. One such fluid contains samples to be analysed while the other fluid contains reagents used in the analysis.

When used to perform a PCR and LCR and any other like reaction, the conduit is also filled with a carrier fluid which is any synthetic based oil that is completely free of any RNA or DNA. Typically, silicon oil is suitable for use in this device. When the device is used in the amplification of nucleic acids, it is vital that such a carrier fluid be used. This is because contamination by even one molecule from a previous sample will cause unacceptable cross contamination since that molecule will also be amplified. In addition, the reaction mixture is run through the conduit under a back pressure to stop the degassing of samples during the heating process.

In practice, individual reaction mixtures are separated by a portion of carrier fluid. In the case of the PCR and LCR, it is vital that cross contamination be avoided. Therefore, in order to prevent mixing of one reaction mixture with a subsequent reaction mixture, it is necessary that each reaction mixture is sequentially injected into the carrier fluid at regular spacings. As a guide, spacing between samples is suitably achieved by setting a distance which is approximately 5 times the internal diameter of the tube between reactants.

The means for causing fluid to be transported through the conduit is for example any suitable pump means. This may comprise a peristaltic pump, for example. It is important that such a means for pumping fluid through the conduit is a precision pump for the reasons described below.

Suitably, the heat exchanger body is any body which is so shaped that it can conveniently accommodate a conduit disposed thereon. It is preferably substantially cylindrically shaped. However, any generally regular, three dimensional shaped body which can accommodate conduit to effectively transfer heat to a fluid in the conduit would be acceptable, provided that its shape permits disposition of conduit on the surface of the heat exchanger in a regular, repeating fashion, each repeat representing one temperature cycle in the case of the device being used in a cyclic reaction.

Suitably, the heat exchanger body has a groove machined into the surface accommodating the conduit and is dimensioned such that it can accommodate the conduit in a close fitting manner. The reason for this groove is to increase the efficiency of heat transfer from the heat exchanger body to the conduit and hence to the fluid therein. In certain reactions to which this device is applicable, for example the PCR and LCR, it is vitally important that ideally no cross contamination between samples occurs. Even if some contamination between samples does occur it is important that this be kept to an absolute minimum. In order to achieve no or minimal contamination, there is provided an injector means.

Thus, in accordance with a fourth aspect of this invention there is provided an injector means for use in a thermal cycling device comprising: a septum; a needle which is able to pierce the septum; a reservoir in fluid contact with the septum, having an inlet and an outlet, and able to accommodate a purge fluid which is able to enter the reservoir via the inlet and leave the reservoir via the outlet; wherein when in use, the needle passes through fluid in said reservoir and then through the septum.

In a preferred form, the injector means comprises a septum and is suitably a rubber septum of the type used in gas chromatography. Another component of the injector is a needle which pierces the septum. Cross contamination is prevented by filling a reservoir above the septum with purge fluid, urging the needle through the reservoir of fluid then through the septum while continually purging the area with purge fluid, withdrawing the needle and finally purging the withdrawn needle prior to its subsequent penetration of the septum with the next sample.

Purge fluid may be silicon oil or PCR grade water or any synthetic oil which is devoid of RNA or DNA.

The septum is made of material which closes about the hole made by a previous penetration. It is preferably made of rubber that is, silicon rubber or natural rubber and is more preferably the same material used in gas chromatography. It is also important, that when back pressure is applied, the septum is of a material which can withstand such back pressure.

Any carry over from the last sample will potentially result in a false positive in the following sample. To overcome this, a negative control is run between each of the samples. Typically, this could be 1 in every 10 samples depending on the characteristics of a particular assay. If the negative control is seen to go positive this would indicate a contamination condition, the entire system could then the purged, both the loading port and the entire spiral tubing, and the last 10 samples (or whatever is considered necessary by the operator) could be re-run and the job continued without intervention. The system could also be flushed with NaOH to degrade any DNA in the system.

When the injector means is used, for example especially in the first and second aspects of this invention, the first fluid is delivered by a first fluid device, that is the injector means described above. The second fluid, transport fluid is delivered by a second fluid device. The transport fluid may be any fluid which is inert and does not interfere with the analysis and furthermore is devoid of DNA and RNA. The transport fluid may be an inert oil and is typically silicon oil. It is preferred that the transport fluid is delivered under pressure, typically between about 700 and 7000 kPa.

As described in our earlier patent (U.S. '183), it is important that back pressure be applied at the end of the fluid stream. As mentioned above, back pressure is suitably between about 300 and about 700 kPa and is achieved by methods known in the art. Specifically, it may be achieved by use of a spring and ball device at the outlet wherein adjusting the tension of the spring sets the pressure. The effect of this is to prevent vaporisation of the fluid stream and reaction mixtures as they pass through the zones of high temperature. As also described in our earlier patent, in order to prevent mixing of reaction mixtures, it is preferred that the flow rate and cross-sectional diameter of the fluid stream are such that turbulent flow is avoided and laminar flow is achieved. Therefore, tubing of small diameter, for example about 3 mm (or ⅛ inch) is particularly preferred since it is both beneficial to rapid heat transfer and minimises turbulent flow. The tube diameter could also be decreased to reduce the reaction volume from 20 μL to 1-2 μL. In this instance the diameter would be about 0.5 mm outside diameter and about 0.2 mm (inside diameter).

In practice, in the case of the present device being used for a PCR, the samples travel along the conduit at a constant velocity (regulated by the precision pump), and so take a known amount of time to complete one revolution. Typically it takes about 1 minute to make a full revolution, and based on a 35 coil system a sample would take 35 minutes to completely flow through the device.

A typical velocity of fluid is 5 mm per second, with a diameter of 100 mm the circumference is approx 300 mm and so a sample takes approx 1 minute for a revolution.

A typical sample volume is 20-50 μL (which, as mentioned above, may be reduced to 1-2 μL) and the length of a sample in the conduit is 5-10 mm. Given that at least 10 readings of the same sample should be taken by the scanner (to be described presently) to obtain an average fluorescent energy, the scan head must scan all coils (typically, 35 coils) in 0.5 seconds. The maximum flow rate will therefore be limited by the scan rate of the scanning head.

A scanning detector, in the case of the heat exchanger body being cylindrical is fitted to the outside of the cylinder and runs from the first coil to the last coil. As the scanning head of the detector moves past each of the coils it detects the fluorescence energy in the conduit. If a sample is present it detects the sample energy, and if only the carrier fluid is present it detects only the background energy of the carrier fluid. The scanning head may be manufactured as an integrated part of the system and multiple is heads may be attached to detect up to 4 channels.

Alternatively, the heat exchanger body itself may be rotated relative to the scanning head. This would allow readings to be taken at different temperature zones by rotating the conduits past the reaction head.

The scanning head suitably consists of a mirror set to direct a laser beam onto the coils, and an optic fibre to collect the fluorescent energy which pipes the collected light to a photomultiplier tube that converts light to a voltage captured by a computer system. On every tenth loading a tracking dye is injected to give a full scale signal so samples order can be maintained in the software. A commercially available scanning head which would be acceptable would be a design similar to the head used in the GS-2000 Gel-Scan. Alternatively, a light source (laser or light emitting diodes) could be mounted on the scanning head.

When the heat exchanger is used in conjunction with the scanning head in order to monitor the progress of reactions occurring in the tubing, it is preferred that the tubing is substantially transparent to fluorescent light emitted from the samples.

Suitable fluorescent dyes are for example, FAM, JOE, and ROX, which are all trademarks of ABI or Cy5.

It is also possible that other detectable methods be used to monitor the course of reaction. For example, any reaction which may be coupled with a reagent where colour change indicates the progress of a reaction would be suitable. Also, chromogenic substrates where suitable, for example chromogenic substrates used in coagulation tests would be suitable.

The device described typically enables a sample to be loaded every 5 seconds into the fluid carrier stream, this equates to automated loading of 18,000 samples in a 24 hour period. The device of this invention therefore has 3 times the throughput, none of the associated robotics for transporting and sealing of plates, and therefore none of the problems associated with such systems.

Optionally, a separate heating device may be added which is placed before the heat exchanger body described above. For example, this may also comprise a cylinder on which the conduit is disposed so that the fluid may be optionally heated prior to its transport to the heat exchanger of the present invention.

BRIEF DESCRIPTION OF THE DRAWINGS

An embodiment of the present invention will now be described with reference to the drawings in which.

BEST AND OTHER MODES FOR CARRYING OUT THE INVENTION

The following describes one embodiment of the present invention which should not be construed as limiting on the scope thereof.

Figure 1:
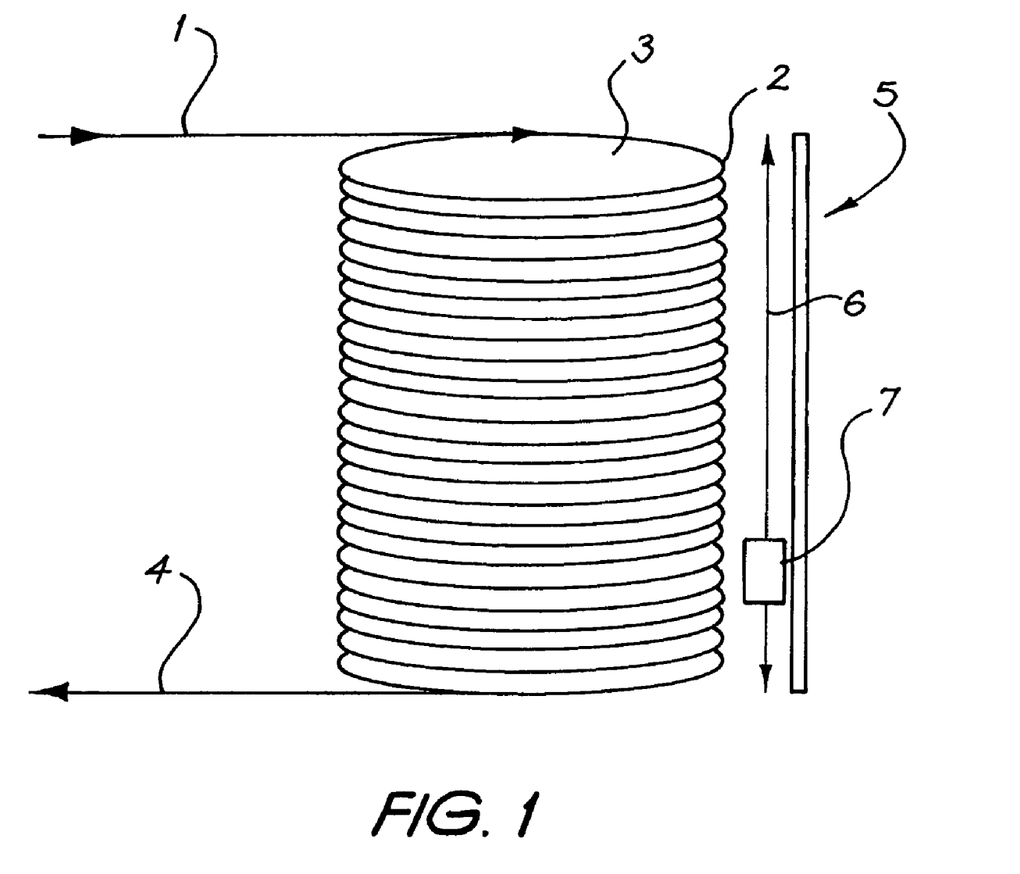
FIG. 1 is a schematic representation of a cylindrically shaped heat exchanger in accordance with the first aspect of this invention used in the PCR together with a schematic representation of the scanner.
Figure 2A:
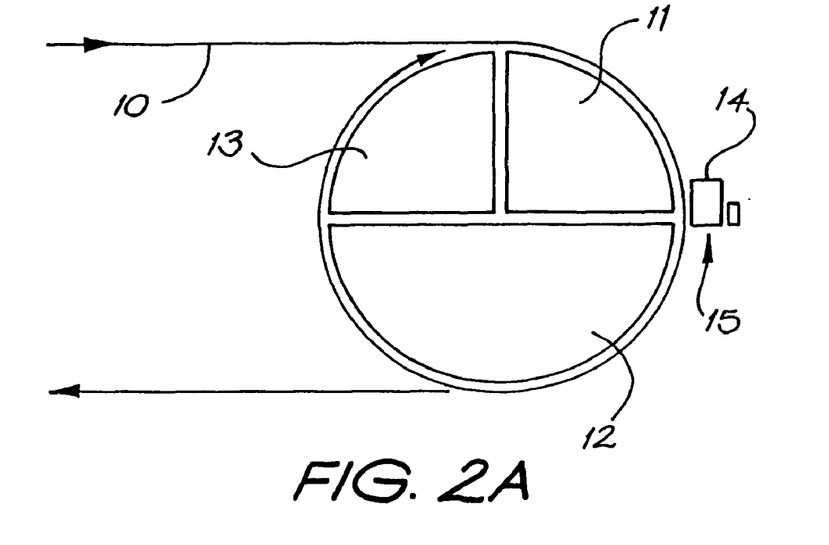
FIG. 2A is a schematic representation of the "pie" shaped segments of the heat exchanger body of FIG. 1.
Figure 2B:
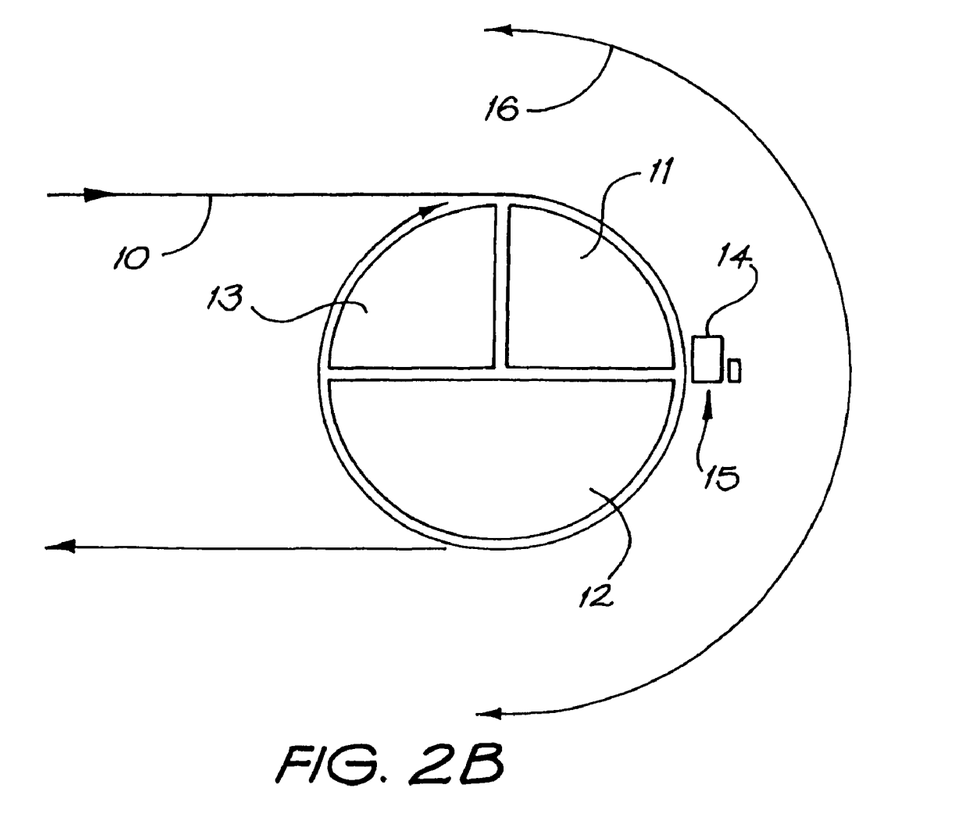
FIG. 2B is a schematic representation of an alternative scanning arrangement of FIG. 2A where the heat exchanger body itself rotates.
Figure 3:
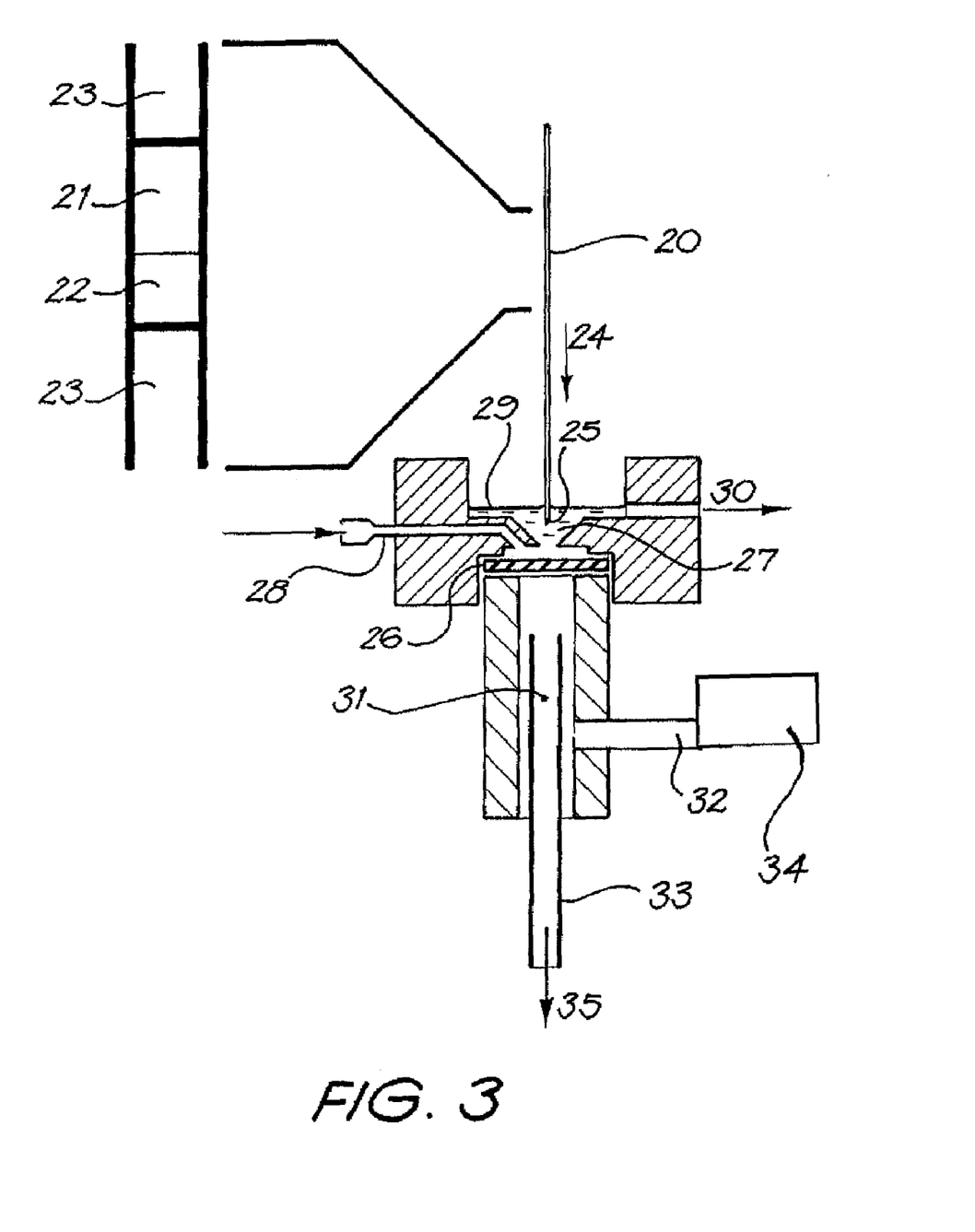
FIG. 3 is a cross section of the injector means.

Conduit 1 carries the reaction mixture which is represented as being delivered by the injector means by arrow 35 in FIG. 3 to the first coil 2 of the heat exchanger body 3 which in FIG. 1 is cylindrically shaped. Heat is transferred from the heat exchanger body 3 to conduit 2 containing the fluid whose temperature then achieves that of the portion of the heat exchanger body adjacent it. The segments of different temperatures are more clearly shown in FIG. 2A and FIG. 2B. The number of turns of conduit disposed on the heat exchanger body represents the number of cycles of nucleic acid amplification. On completion of the desired number of cycles of the amplification reaction, the reaction fluid exits the device by conduit 4. The device may be used preparatively, that is, the fluid may be collected and the amplified nucleic acid isolated; or analytically, that is, the fluid may be analysed. A scanning detector 5 is fitted to the outside of the heat exchanger. The direction of the arrow 6 indicates that the scanning head 7 travels past the coils and detects sample energy emanating from those coils.

Turning to the embodiment depicted in FIG. 2A, again, reaction mixture, represented as being delivered by the injector means by arrow 35 in FIG. 3, enters by conduit 10 and firstly encounters a segment 11 held at approximately 95° C. It is then transported to a zone 12 which is held at 55° C. at which temperature the amplification reaction takes place. The fluid is then transported to the segment 13 held at approximately 72° C. As can be seen from FIG. 2A the fluid passes the head 14 of the scanner detector 15 as fluid leaves segment 11, held at approximately 95° C.

An alternative scanning arrangement is shown in FIG. 2B where the heat exchanger body rotates about its longitudinal axis through 180° approximately. This is indicated by double headed arrow 16. An advantage of this arrangement is that the same scanning head could monitor the reaction in different temperature zones. As a further alternative, the scanning head itself may rotate about the longitudinal axis of the heat exchanger body through 180°, also indicated by the double headed arrow 16. This would also allow the reaction to be monitored in different temperature zones.

The injector means is depicted in FIG. 3. This consists of a needle 20 into which is loaded the reagent mixture comprising reagent 21 and nucleic acid sample 22. This reaction mixture is separated from the preceding mixture and following mixture by carrier fluid 23. When loading the sample into the conduit, the reaction mixture is pumped down the needle by means of a pump (not shown) in the direction of arrow 24 through tip 25. Prior to piercing septum 26, the needle is washed by purge fluid which is situated in reservoir 27. The purge fluid is introduced into the reservoir 27 by an inlet 28 and is maintained at a height 29 due to outflow of purge fluid through outlet 30 when the needle 20 pierces septum 26, the pump (not shown) expels the contents of needle 20 into the conduit by stopping at position 31 whereupon the contents are expelled into a constantly flowing stream of transport oil which enters conduit 33 at position 32. The reaction mixture and transport oil are then transported under the pressure of the oil inlet pump schematically represented at 34. The mixture is transported to the heat exchanger body in the direction of arrow 35 and undergoes cycles of amplification on the body represented in FIGS. 1 and 2. The number of cycles is determined by the number of windings of conduit chosen by the operator.

Figure 4:
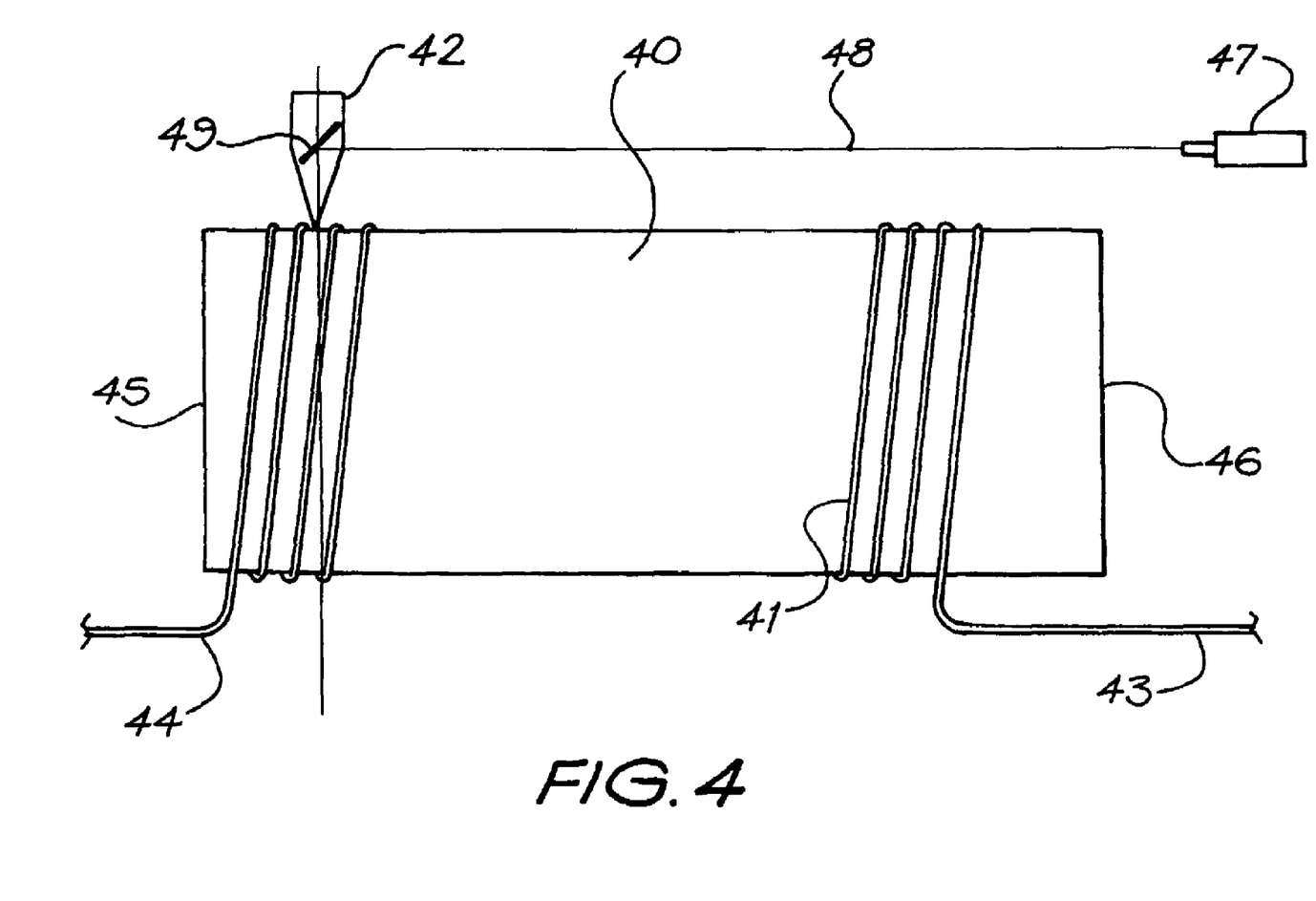
FIG. 4 is a schematic representation of a cylindrically shaped heat exchanger in accordance with the second aspect of this invention.

A further embodiment of this invention is depicted in FIG. 4. The reaction mixture, represented as being delivered by the injector means by arrow 35 in FIG. 3 enters the device by conduit 44. The heat exchanger body includes a solid aluminium rod 40 on which is wound a series of coils of conduit 41. The method will be further exemplified in Example 2. In this example, the temperature at which the reaction mixture in the conduit arrives at the heat exchanger body at end 45 is 50° C. and the final temperature at end 46 is 95° C. Thus, it is possible to select a temperature gradient along the longitudinal axis of the heat exchanger body. Since temperatures in this reaction may cause degassing, a back pressure is applied at position 43. The scanning device 42 includes a laser source 47 which transmits a laser beam 48 to a beam splitter 49. The resulting fluorescence caused by the reaction in the conduit is detected by detector 42 and analysed by methods known in the art. The scanner is able to move along the outside of the heat exchanger and can monitor the course of the reaction at any point.

Figure 5:
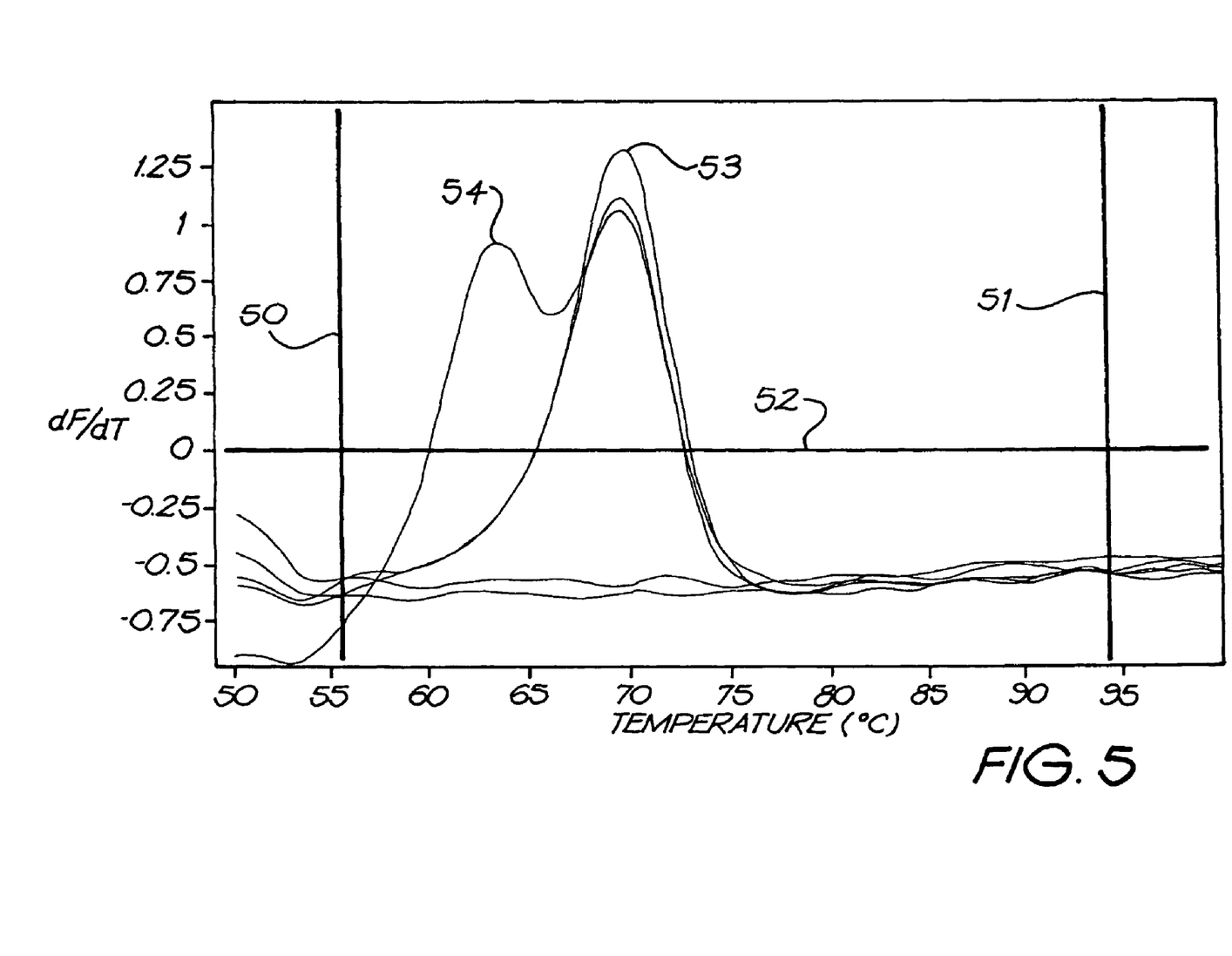
FIG. 5 shows the results of a DNA melt experiment using the device schematically represented in FIG. 4.

FIG. 5 shows a typical DNA melt detection analysis. The x-axis represents temperature and the y-axis represents dF/dT which is the change in fluorescence compared to change in temperature. The vertical line 50 in the graph represents the left hand side of the device 40 in FIG. 4 while the vertical line 51 represents the right hand side of the device 40 in FIG. 4. Horizontal line 52 in the graph represents the threshold level determined by computer representing signal above the noise level. The peak at 69° C. (ie reference numeral 53) represents wild type DNA; the peaks at 62° C. and 69° C. (ie reference numerals 54 and 53 respectively) represent heterozygous DNA; and the peak at 62° C. (ie reference numeral 54) represents a mutation in the DNA.

Figure 6:
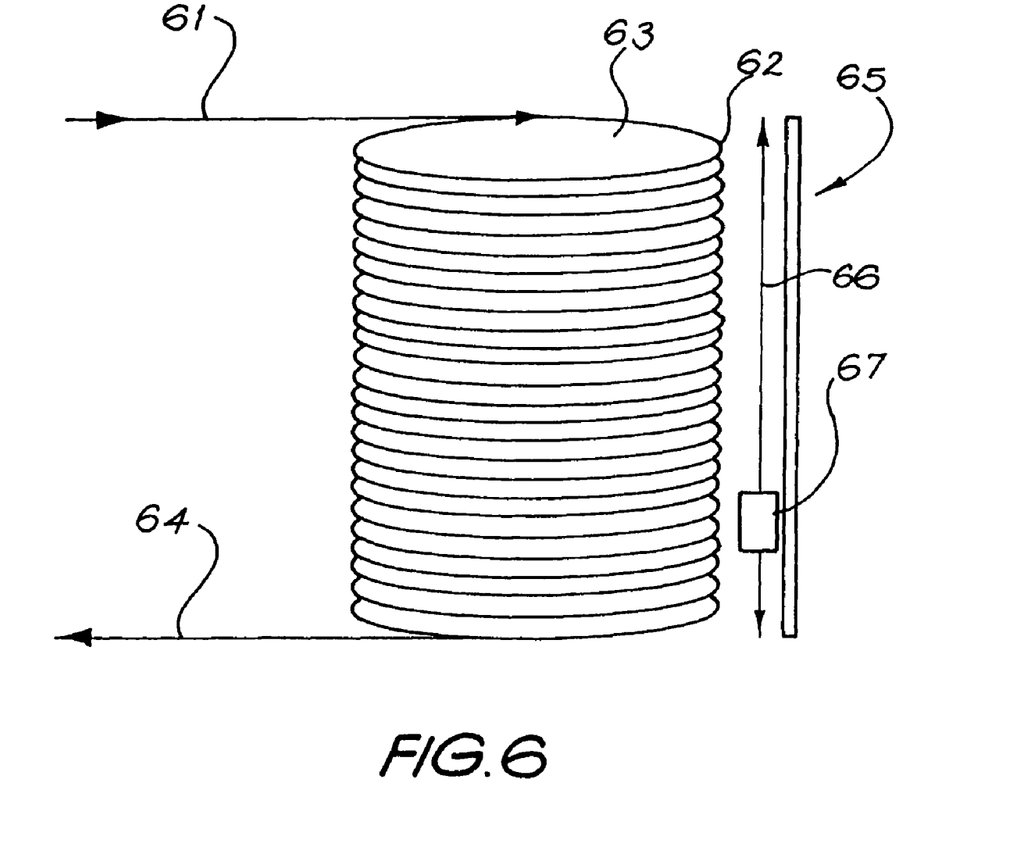
FIG. 6 is a schematic representation of a cylindrically shaped isothermal device in accordance with the third aspect of this invention.

FIG. 6 illustrates the isothermal device of the third aspect of this invention. Conduit 61 carries the reaction mixture which is represented as being delivered by the injector means by arrow 35 in FIG. 3 to the first coil 62 of the heat exchanger body 63 which in FIG. 6 is cylindrically shaped. In this aspect of the invention, the fluid which enters conduit 61 consists of a mixture of two fluids namely an antigen and an antibody to the antigen which have been mixed prior to entering conduit 61. Heat is transferred from the heat exchanger body 63 to conduit 62 containing the fluid whose temperature then achieves that of the heat exchanger body. The number of turns of conduit disposed on the heat exchanger body, together with the flow rate of fluid in conduit 61, dictates the reaction time. On completion of the reaction, the reaction fluid exits the device by conduit 64. A scanning detector 65 is fitted to the outside of the heat exchanger. The direction of the arrow 66 indicates that the scanning head 67 travels past the coils and is able to monitor the reaction taking place therein. In this aspect of the invention, it is not as important as in the first aspect of the invention to prevent cross contamination and therefore, it is not vital that the injector means be used. In addition, since reactions between antigens and antibodies are normally carried out at approximately 45° C., degassing will not occur and therefore it is not essential to apply a back pressure to the fluid leaving the device.

The invention is further illustrated by way of the following examples which are not to be construed as limiting on the scope of the invention thereof.

EXAMPLE 1

Operation of Injection System

The following example illustrates the operation of an injection system with the dimensions and parameters set out below.

(A) Injection
(1) The needle is purged with silicon carrier oil.
(2) Sample and reagent are then loaded onto the needle (typically 2-50 µL), then carrier oil is loaded into the needle (typically 10-100 µL).
(3) The needle is placed over the injection port, pushed down through the rubber septum, and into the 1/16 PTFE tubing that carries the main oil flow.
(4) The contents off the needle are then injected into the oil stream and the needle is removed from the injector ready to load another sample.

(B) Purging: The purpose of the purge fluid (oil or water flow) is to clean the outside surface of the needle before it passes through the septum. The purge flow is in reverse to that of the needle movement in that the flow comes up from the septum to waste.

(C) Oil Inlet from Pump: A high pressure (typically about 700- about 7000 kPa, that is about 100- about 1000 psi) constant flow pump is used to regulate the main carrier oil flow through the injector port that is coupled to the real-time flow through heating system.

EXAMPLE 2

DNA Melt Detection Assay

To detect DNA point mutations it is standard practice to design a synthetic piece of DNA (oligo probe typically a 20 mer) that spans the mutation site. If the probe has been designed to be 100% homologous to the wild type (normal) then these samples will have a higher melting point. For example, when the same probe hybridizes to a mutated DNA sample, there is a base mismatch and the probe is not 100% homologous and so the thermal energy required to denature the probe from the DNA target is less which produces a lower melting point. Thus by comparing melting points of different DNA samples it is possible to determine whether the sample is normal or a mutation.

Thus, DNA melt detection is carried out using one embodiment of the invention. Reference is made to FIG. 4 which schematically illustrates use of the heat exchanger in this method. That is, the heat exchanger body is heated at one end at approximately 50° C. and at the other end at approximately 95° C. The temperature gradually changes over the length of the cylinder. In this instance, 45 turns give approximately 1° C. difference. That is, each turn is 1° C. hotter than the turn before it. FIG. 5 is a DNA melt experiment using the apparatus of FIG. 4 where the temperature is adjusted in accordance with the second aspect of this invention. The higher temperature peak in FIG. 5 is wild type DNA and the lower temperature peak is mutated DNA

INDUSTRIAL APPLICABILITY

It should be clear that the present invention will find wide applicability in laboratories where preparative and analytical amplification of nucleic acids is carried out.

Modifications obvious to those skilled in the art may be made without departing from the scope of the present invention.

The invention claimed is:

1. A thermal cycling device comprising:
   a heat exchanger body having a longitudinal axis and longitudinally divided to provide at least two segments which are able to be heated to different temperatures so that said body has peripheral surfaces of different temperatures;
   a conduit wound about said body so as to be in thermal contact with said peripheral surfaces;
   a first delivery device to deliver a first fluid to said conduit to cause said fluid to pass therealong and therefore change in temperature as the fluid passes said segments;
   a second delivery device to deliver a second fluid to said conduit so as to flow with said first liquid and therefore also change in temperature; and
   a scanning detector configured to monitor the course of a reaction occurring in said conduit by scanning individual windings of said conduit.

2. The device according to claim 1 wherein the body is divided into 3 segments able to be heated to different temperatures.

3. The device according to claim 2 wherein the circumferential proportion of the segments is 1:2:1.

4. The device according to claim 3 wherein the temperatures in each segment are: (a) about 94° C., (b) about 55° C., and (c) 72° C. respectively.

5. The device according to claim 1 wherein the first fluid comprises a sample to be analysed and reagents used in the analysis and the second fluid comprises a transport fluid.

6. The device according to claim 5 wherein a sample to be analysed is separated from a following sample to be analysed by a carrier fluid to substantially prevent contamination between said samples.

7. The device according to claim 6 wherein the carrier fluid is silicon oil, PCR grade water or any synthetic oil which is devoid of RNA or DNA.

8. The device according to claim 5 wherein the sample to be analysed comprises at least one nucleic acid.

9. The device according to claim 8 wherein the analysis is the polymerase chain reaction or the ligase chain reaction.

10. A thermal cycling device comprising:
    a heat exchanger body having a longitudinal axis and transversely divided to provide at least two segments which are able to be heated to different temperatures so that said body has peripheral surfaces of different temperatures;
    a conduit wound about said body so as to be in thermal contact with said peripheral surfaces;
    a first delivery device to deliver a first fluid to said conduit to cause said fluid to pass therealong and therefore change in temperature as the fluid passes said segments;
    a second delivery device to deliver a second fluid to said conduit so as to flow with said first liquid and therefore also change in temperature; and
    a scanning detector configured to monitor the course of a reaction occurring in said conduit by scanning individual windings of said conduit.

11. The device according to claim 10 wherein a temperature gradient is applied across the at least two segments.

12. The device according to claim 11 wherein the temperature gradient is from about 50° C. to about 95° C.

13. The device according to claim 10 wherein the first fluid comprises a sample to be analysed and the second fluid comprises a transport fluid.

14. The device according to claim 13 wherein the sample comprises a nucleic acid.

15. The device according to claim 14 wherein the analysis is a nucleic acid melt detection assay.

16. An isothermal device comprising:
    a heat exchanger body having a longitudinal axis and a peripheral surface and being adapted to maintain the temperature of said peripheral surface at a constant selectable temperature;
    a conduit wound about said body so as to be in thermal contact with said peripheral surface;
    a first delivery device to deliver a first fluid to said conduit to cause said fluid to pass therealong and therefore change in temperature as the fluid passes said peripheral surface;
    a second delivery device to deliver a second fluid to said conduit so as to flow with said first liquid and therefore also change in temperature; and
    a scanning detector configured to monitor the course of a reaction occurring in said conduit by scanning individual windings of said conduit.

17. The device according to claim 16 wherein the first fluid comprises an antibody and an antigen to said antibody and the second fluid comprises a transport fluid.

18. The device according to claim 17 used to analyse an antibody-antigen binding reaction.

19. The device according to claim 1, 10 or 16 wherein said body is a regular, three dimensional shaped body which can accommodate conduit to effectively transfer heat to a fluid in the conduit.

20. The device according to claim 19 wherein said body is cylindrically shaped.

21. The device according to claim 19 wherein said body has a groove in the surface to accommodate the conduit in thermal contact with said surface.

22. The device according to claim 19 wherein said conduit extends angularly about said body relative to said axis.

23. The device according to claim 19, where said conduit extends about said body in a series of consecutive windings.

24. The device according to claim 23 wherein the number of windings is between about 35 and about 60.

25. The device according to claim 24 wherein the number of windings is about 60.

26. The device according to claim 1, 10 or 16 wherein said conduit is tubing which is able to conduct heat from said heat exchanger body to fluid in said conduit so that a selectable change in temperature in a segment of said heat exchanger body accurately causes a selectable change in temperature in a particular portion of said conduit adjacent that portion of said heat exchanger body.

27. The device according to claim 26 wherein the interior surface of the conduit is hydrophobic.

28. The device according to claim 27 wherein the conduit is PTFE tubing or a similar tubing.

29. The device according to any one of claim 5, 13 or 17 wherein the transport fluid is delivered under pressure.

30. The device according to claim 29 wherein the pressure is from about 700 to about 7,000 kPa.

31. The device according to claim 1, 10 or 16 wherein a back pressure is applied at the end of the fluid stream.

32. The device according to claim 31 wherein the back pressure is between about 300 and about 700 kPa.

33. The device according to claim 1, 10 or 16 wherein the body is hollow.

34. The device according to claim 1, 10 or 16 wherein the body is solid.

35. The device according to claim 1, 10 or 16 comprising heating and/or cooling means to achieve a selectable temperature.

36. The device according to claim 35 wherein the heating device is a Peltier device.

37. The device according to claim 1, 10 or 16 further including injector means.

38. The device according to claim 37 wherein the first fluid is delivered by the injector means.

39. The device according to claim 38 wherein a marker reagent for monitoring a chemical reaction in said conduit is added to at least one of said first and second fluids.

40. The device according to claim 39 wherein said marker reagent is a fluorescent dye, a coupling reagent where a change in colour indicates progress of a reaction, or a chromogenic substrate.

41. The device according to claim 1, 10 or 16, wherein said scanning detector is able to move past successive windings of said conduit, thereby to detect the course of a reaction in the conduit by scanning an individual winding of said conduit and analysing.

42. The device according to claim 1, 10 or 16 wherein said heat exchanger body is able to move relative to the scanning detector, thereby to detect the course of a reaction in the conduit by scanning an individual winding of said conduit and analysing.

43. A nucleic acid prepared by using the device according to any one of claim 1, 10 or 16.

44. The device according to any one of claim 1, 10 or 16, wherein said scanning detector is fixed at each winding of said conduit, thereby to detect the course of a reaction in the conduit by scanning an individual winding of said conduit and analysing.

45. The device according to claim 1,10 or 16 wherein said scanning detector comprises at least one scanning head.

46. The device according to claim 45 wherein said scanning head is adapted to direct light onto said conduit and includes an optic fiber to collect fluorescent energy.

* * * * *